United States Patent
Heidaran et al.

(10) Patent No.: US 6,849,606 B2
(45) Date of Patent: Feb. 1, 2005

(54) METHOD OF INDUCING OR ENHANCING CHONDROGENESIS WITH EXTRACELLULAR MATRIX CONTAINING GDF-5

(75) Inventors: Mohammad A. Heidaran, Los Gatos, CA (US); Robert C. Spiro, Half Moon Bay, CA (US); Robin Daverman, Campbell, CA (US); LinShu Liu, Sunnyvale, CA (US)

(73) Assignee: Depuy Spine, Inc., Raynham, MA (US)

( * ) Notice: Subject to any disclaimer, the term of this patent is extended or adjusted under 35 U.S.C. 154(b) by 0 days.

(21) Appl. No.: 10/444,640

(22) Filed: May 22, 2003

(65) Prior Publication Data

US 2003/0207816 A1 Nov. 6, 2003

Related U.S. Application Data

(63) Continuation of application No. 09/418,689, filed on Oct. 14, 1999, now Pat. No. 6,586,406.
(60) Provisional application No. 60/104,220, filed on Oct. 14, 1998.

(51) Int. Cl.$^7$ .............................................. A61K 38/00
(52) U.S. Cl. .............................. 514/21; 514/21; 514/12; 514/2; 514/8; 530/350; 530/300; 530/356
(58) Field of Search ............................... 514/21, 12, 2, 514/8; 530/350, 300, 356

(56) References Cited

U.S. PATENT DOCUMENTS

| | | | |
|---|---|---|---|
| 4,703,108 A | 10/1987 | Silver et al. ................. 530/356 |
| 4,975,526 A | 12/1990 | Kuberasampath et al. .. 530/350 |
| 5,055,298 A | 10/1991 | Kludas ....................... 530/350 |
| 5,118,667 A | 6/1992 | Adams et al. ................. 514/12 |
| 5,204,325 A | 4/1993 | Lindstrom et al. ............. 514/4 |
| 5,208,219 A | 5/1993 | Ogawa et al. .................. 514/2 |
| 5,356,629 A | 10/1994 | Sander et al. ................ 424/422 |
| 5,413,989 A | 5/1995 | Ogawa et al. ................. 514/12 |
| 5,801,014 A | 9/1998 | Lee et al. .................... 435/69.1 |
| 6,683,064 B2 * | 1/2004 | Thompson et al. ............ 514/54 |

OTHER PUBLICATIONS

Oxford Dictionary of Biochemistry and Molecular Biology, Oxford University Press, Oxford, 1997 pp. 125–126.
Hotten et al., "Recombinant Human Growth/Differentiation Factor 5 Stimulates Mesenchyme Aggregation and Chondrogenesis Responsible for the Skeletal Development of Limb", Growth Factors, vol. 13, pp. 65–74, 1996.
Docherty et al., "Glycosaminoglycans Facilitate the Movement of Fibroblasts Through Three–Dimensional Collagen Matrtices", Journal of Cell Science, vol. 92, pp. 263–270.
Hall & Miyake, "Divide, Accumulate, Differentiate: Cell Condensation in Skeletal Development Revisited", International Journal of Development Biology, vol. 39, pp. 881–893, 1995.
Iwasaki et al., "Regulation of Proliferation and Osteochondrogenic Differentiation of Periosteum–deived Cells by Transforming Growth Factor–Beta and Basic Fibroblast Growth Factor", Journal of Bone and Joint Surgery, vol. 77, (4), pp. 543–554, 1995.
Kawasaki et al., "Hyaluronic Acid Enhances Proliferation and Chondroitin Sulfate Synthesis in Cultured Chondrocytes Embedded in Collagen Gels", Journal of Cellular Physiology, vol. 179, pp. 142–148, 1999.
PCT International Search Report, PCT/US99/24130, Feb. 8, 2000.
Heidaran et al., "Extracellular Matrix Modulation of rhGDF–5–Induced Cellular Differentiation", e–biomed, vol. 2, Sep. 2000.
Massague, Joan, The TGF–β Family Growth and Differentiation Factors, Cell, vol. 49, No. 4, May 1987.

* cited by examiner

Primary Examiner—Jon Weber
Assistant Examiner—Hope A. Robinson
(74) Attorney, Agent, or Firm—Beyer Weaver & Thomas, LLP.

(57) ABSTRACT

A method and composition are provided for inducing or enhancing chondrogenesis in vivo or in vitro. The method is performed by exposing the cells in vitro or in vivo to an extracellular matrix comprising of type I collagen, type II collagen or a mixture of type I collagen or type II collagen and hyaluronate and further containing GDF-5.

3 Claims, No Drawings

METHOD OF INDUCING OR ENHANCING CHONDROGENESIS WITH EXTRACELLULAR MATRIX CONTAINING GDF-5

This is a Continuation application of prior application Ser. No. 09/418,689 filed on Oct. 14, 1999, now U.S. Pat. No. 6,586,406, which claims benefit of 60/104,229 filed Oct. 14, 1998.

BACKGROUND OF THE INVENTION

The limited capacity of articular cartilage to regenerate represents a major obstacle in the management of degenerative and traumatic joint injuries. The maintenance of a functional joint surface requires that articular chondrocytes respond to extracellular signals that are generated from growth and differentiation factors, mechanical stimuli, and interactions with specific components of the extracellular matrix. The invention is directed to an extracellular matrix of type I collagen, type II collagen, type I collagen plus hyaluronate, or type II collagen plus hyaluronate, and differentiation factor-5 (GDF-5), a member of the bone morphogenetic protein (BMP) family that is involved in joint development on the chondrogenic activity of growth.

Coordinated function of many cell types is regulated by integration of extracellular signal derived from soluble factors inducing growth factors and insoluble molecules such as extracellular matrix (ECM). The skeletal elements of the vertebrate limb are derived during embryonic development from mesenchymal cells, which condense and initiate a differentiation program that result in cartilage and bone. Bone morphogenetic proteins may play a crucial role in mesenchymal condensations in skeletal patterning, including the process of joint formation. This is based upon in situ hybridization and immunostaining showing that GDF-5 is predominantly found at the stage of precartilaginous mesenchymal condensation and throughout the cartilaginous cores of the developing long bone; and null mutation in GDF-5 (frameshift mutation at the mouse brachypodism locus) resulting in disruption of the formation of approximately 30% of the joints in the limb. This includes the complete absence of joint development between the proximal and medial phalanges in the forefeet and hindfeet. Further evidence of the role of GDF-5 in regulating the cellular condensation required for chondrogenesis and joint formation comes from null mutation of noggin gene which is a known antagonist of bone morphogenetic protein function. While, in mice lacking noggin, cartilage condensation initiated, the process of joint formation failed as judged by the absence of GDF-5 expression.

Despite the importance of joint formation in skeletal patterning and human disease, relatively little is known about the molecular mechanisms that control where and when a joint will form. In the limb, joints typically arise by the splitting of larger skeletal precursors, rather than by collision or apposition of separate elements. This process takes place through a series of steps including: 1) initial formation of specialized regions of high density that extend in transverse stripes across developing cartilage element; 2) programmed cell death and changes in matrix production in the center of the interzone, creating a three layer structure; 3) differentiation of articular cartilage at the two edges of the interzone; and 4) accumulation of fluid-filled spaces that coalesce to make a gap between opposing skeletal elements. Expression of GDF-5 is initiated in the region of joint development 24–36 hours before the morphological appearance of the interzone. The expression continues for at least 2–3 days at a particular site, and is still evident at the three-layered interzone stage of joint development. The expression level of GDF-5 then decreases at later stages of joint formation. In vitro biological and biochemical analyses of recombinant hGDF-5 suggest that the primary physiological role of GDF-5 may be restricted to early stages of chondrogenesis of mesenchymal progenitor cells. This is based on a showing that: 1) GDF-5 stimulates mesenchymal aggregation and chondrogenesis in rat limb bud cells; 2) GDF-5 fails to stimulate alkaline phosphatase activity measured utilizing well differentiated osteoblastic cell type MC3T3-E1 cells; 3) GDF-5 stimulates alkaline phosphatase activity in rat osteoprogenitor cells ROB-C26 which is more primitive and less differentiated; 4) GDF-5 binds to distinct heterodimer of receptor for BMPs which is expressed more prevalently in less differentiated cells of mesenchymal origin.

SUMMARY OF THE INVENTION

This invention is directed to a method and composition for inducing or enhancing chondrogenesis in cells or tissue with an extracellular matrix containing GDF-5. The extracellular matrix consists of type I collagen or type II collagen and contains growth and differentiation factor-5, GDF-5. An effective amount of GDF-5 to induce or enhance chondrogenesis is about 1 ng to 10 mg/ml matrix protein. A matrix is a solid porous composition having a relatively fixed three-dimensional structure.

DESCRIPTION OF THE PREFERRED EMBODIMENTS

Chondrogenesis is induced by an extracellular matrix composition of type I collagen, type II collagen, type I collagen plus hyaluronate, or type II collagen plus hyaluronate containing GDF-5. Type I and II collagen represent the most abundant ECM protein in bone and cartilage, respectively.

Collagen may be obtained from bone, tendons, skin, or the like. The collagen source may be any convenient animal source, mammalian or avian, including bovine, porcine, equine, or the like, or chicken, turkey or other domestic source of collagen.

Hyaluronic acid is a naturally-occuring polysaccharide containing alternating N~acetyl~D~glucosamine and D~glucuronic acid monosaccharide units linked with beta 1–4 bonds and disaccharide units linked with beta 1–3 glycoside bonds. It occurs usually as the sodium salt and has a molecular weight range of about 50,000 to $8 \times 10^6$.

The collagen or collagen-hyalurate mixture is provided as a matrix, typically by lyophilization. The collagen-hyaluronate is formed by treating collagen with an active formyl aldehyde hyaluronate, formed as described in U.S. Pat. No. 5,866,165, incorporated by reference herein. The collagen hyaluronate composition is also provided as a matrix by lyophilization.

The matrix is preferably implanted with an effective amount of GDF-5, which is about 1 mg to 10 mg/ml of matrix protein.

To show in vitro application, fetal rat calvarial cells (FRC's) were plated on various purified extracellular matrix proteins in the presence of recombinant human GDF-5 (100 ng/ml) for 3 weeks and scored for differentiation at the level of morphology, overall proteoglycan synthesis and deposition, and aggrecan and type II collagen expression.

Results show that GDF-5 stimulated chondrogenic nodule formation of FRC's plated only on type I or type II collagen. Chondrogenic nodules stained heavily with alcian blue and were positive for type II collagen and aggrecan-expression, as judged by immunohistochemical and transcriptional analyses. Cells in monolayer that surround the nodules were negative for the chondrogenic markers. In sharp contrast, GDF-5 failed to stimulate chondrogenesis in FRC's plated on fibronectin, type IV collagen or tissue culture plastic.

Plastic plates were first coated with different ECM proteins including type I and II collagen, type IV collagen, or fibronectin. The results show that GDF-5 stimulated the formation of chondrogenic cell aggregate that bind heavily to the alcian blue stain. Under these conditions GDF-5 fails to stimulate the formation of characteristic nodules in FRC cultured in the presence of vehicle alone, type IV collagen, or fibronectin. Plastic culture 12 well (Costar, Cambridge, Mass.) were coated with 0.01% (w/v) of the indicated extracellular matrix proteins for 2 hours at 37° C. After removal of nonadsorbant protein, fetal rat calvarial cells were plated at a density of $2 \times 10^5$ cells/well in DMEM containing 10% FBS. Culture plates were then maintained for 21 days in culture media supplemented with or without GDF-5 (100 ng/ml). Plates were then stained overnight with alcian blue stain (0.5% w/v in 3% acetic acid), washed and photographed. For quantitation of alcian blue, cells were solubilized in 8M urea, and the amount of stain was quantitated using spectrophotometer (Molecular Devices, Sunnyvale, Calif.). Since alcian blue is a cationic dye which has been shown to bind to anionic proteins including proteoglycans, these results suggest that GDF-5 induces a change in cellular morphology of a subpopulation of FRC.

To examine correlation of changes in cellular morphology with the process of chondrogenesis, total cellular RNA and protein were isolated from FRC culture treated with GDF-5 in the presence of type I collagen. Total cellular RNA isolated from FRC cells was subjected to a semiquantitative PCR analysis using specific primers designed to amplify aggrecan, type II collagen or type I collagen. Results show that expression of type II collagen and aggrecan mRNA is increased by around 2 and 3 respectively in cultures treated with GDF-5. Under these conditions, type I collagen mRNA expression decreased by about 20%. The expression of aggrecan and type II collagen was confirmed using slot blot analysis.

Total cell lysates (100 ug) were electrophoretically separated on a 8% or 5% SDSPAGE, transferred to immobilon-P and immunoblotted using antibody specific to type II collagen or aggrecan. The results show that GDF-5 stimulated a significant increase in the steady state level of type II collagen and aggrecan. Under these conditions GDF-5 fails to stimulate expression of type II collagen or aggrecan when FRC cells are cultured in the absence of type I collagen.

The collagen is also provided in matrix form for in vivo use. Type I collagen fibers were dispersed at 2% weight % ratio in distilled water and homogenized 3 times for 5 seconds each at low speed in a heavy duty blender. The pH of the slurry was then adjusted to a) pH 3.0; b) pH 70; or c) pH 10.0 by adding HCl or NaOH as necessary. The slurry was then cast into molds and frozen at the following temperatures prior to lyophilization:

a) pH 3.0 slurry: −78° C., −40° C. or −20° C.
b) pH 7.0 slurry; −40° C.
c) ph 10.0 slurry; −40° C.

The lyophilization cycle for the above matrices was as follows: 0° C. for 2 hours; −40° C. for 2 hours; −20° C. for 2 hours; −4° C. for 4 hours; and 25° C. for 1 hour.

Hyaluronate containing active formyl aldehyde groups, prepared as disclosed in U.S. Pat. No. 5,866,165, was added to the above collagen matrices by immersion of the collagen matrix in a 2% weight % solution, pH 7–8 of the hyaluronate polyaldehyde. The immersed matrices were shaken at room temperature for 4 hours, washed 3 times and lyophilized using the lyophilization cycle described above for the collagen matrix preparation.

A porous matrix fabricated from type I collagen was seeded by, $1 \times 10^5$ cell per implant ($2 \times 3 \times 3$ mm). Cells embedded in matrices were then cultured for 3 weeks in culture supplemented with or without GDF-5 (100 ng/ml). Total RNA isolated from each implant were then subjected to RT-PCR. Results indicate that GDF-5 induced expression of aggrecan and type II collagen, two well known markers of chondrogenesis. In parallel the implant material was subject to histological evaluation followed by alcian or Toludine blue staining. Results show that GDF-5 was capable of inducing marked changes in cellular morphology of FRC underscored by increase in alcian blue staining and changes in cell shape. Under these conditions FRC cells were not able to proliferate and differentiate in the ECM in the absence of GDF-5 as measured by histological evaluation total DNA, RNA or protein content. These findings suggest that the GDF-5 biological response may be significantly enhanced by type I collagen possessing 3D matrix structure.

The surface property or the porosity of 3D collagen-based matrices were examined by preparing a series of implantable material possessing different porosity. Each matrix composite was either coated with or without hyaluronic acid, a major component of cartilage. The implants were then seeded with $1 \times 10^5$ cells per implant and cultured for 3 weeks in the presence of GDF-5 (100 ng/ml). Total RNA extracted from each implant were then subjected to semi-quantitative PCR analysis. Results indicate that FRC cells showed significant increase in the expression level of type II collagen and aggrecan when implanted only in matrices which were coated with hyaluronic acid and possessed the highest porosity (about 300 micron). Together these findings indicate that GDP-5 chondrogenesis activity is fully and potently synergized by a matrix which contain 1) high pore size (about 100–300 micron); and 2) is composed of type I collagen which is coated with hyaluronic acid.

The molecular signaling mechanism by which GDF-5 induces chondrogenesis in the context of type I collagen was also examined using well-characterized inhibitors of intracellular signaling mediators. Results show that the ligand-dependent chondrogenesis was completely inhibited by the calcium ionophore A23187 and rapamycin not by dibutyryl-cAMP, $Na_3VO_4$, or EGTA. The known inhibitory effect of rapamycin on activation of p70S6 kinase indicate that GDF-5/type I collagen-induced chondrogenesis is mediated through p70S6 kinase activation. The known effects of A23187 on intracellular calcium concentrations suggest that the GDF-5/type I collagen-induced chondrogenesis is mediated through a sustained decrease of intracellular calcium concentration.

These results indicate that cellular interaction with type I collagen significantly enhances the chondro-inductive activity of GDF-5. This effect is likely mediated by the convergence of downstream matrix and factor receptor signaling pathways.

The data indicates that GDF-5 biological function is modulated by a type I collagen extracellular matrix composition and structure containing GDF-5 that this event is regulated both temporally and spatially whereby one may regulate cellular morphogenesis and joint development in vivo.

The growth and differentiation factor-induced chondrogenesis is highly specific to GDF-5. It was shown that ECM-dependent chondrogenesis by GDF-5 is highly specific, by evaluating the ability of several mitogens and prototype differentiation factors under the following conditions. Chondrogenesis was assessed by monochromatic staining of FRC cultured in the presence of type I collagen and various growth factors. The results show that crude preparations of BMPs and TGFb, two other member of this class of differentiation factors, completely failed to stimulate chondrogenesis. In addition, growth factors including bFGF or IGF-I, IGF-II failed to stimulate chondrogenesis under these conditions. Together these findings suggest that the GDF-5 biological response may be distinguished from that shown by other members of TGFb superfamily.

EXAMPLE

In vivo activity of rhGDF-5 on collagen-based matrices. Collagen/hyaluronan matrices (CN/HA) loaded with rhGDF-5 (1,5 and 50% g) and implanted intramuscularly in rats for 14 days resulted in a dose-depended increase in alkaline phosphatase activity and chondrogenesis. Under these conditions, very little evidence of chondrogenesis and full terminal differentiation was detected with mineralized collagen combined with rhGDF-5.

| IMPLANT (n = 4 per group) | ALP activity (intramuscular) (mean ∓ SD) |
|---|---|
| CN/HA | 0.82 – 0.27 |
| +1 µg rhGDF-5 | 3.25 ∓ 0.76 |
| +5 µg rhGDF-5 | 20.8 ∓ 7.23 |
| +50 µg rhGDF-5 | 48.9 ∓ 11.3 |
| Mineralized Collagen Matrix | 0.77 ∓ 0.55 |
| +1 µg rhGDF-5 | 0.89 ∓ 0.20 |
| +5 µg rhGDF-5 | 2.68 ∓ 0.30 |
| +50 µg rhGDF-5 | 6.21 ∓ 1.67 |

ALP activity = nmoles/min/mg wet wgt.implant

Method:

In vivo assays, rat soft tissue implants: Matrix/growth factor combinations were implanted either subcutaneously in the thoracic region or intramuscularly in posterior tibial muscle pouches created by blunt dissection in 8 week old male Sprague-Dawley rats. At 14 days post-surgery, implants were harvested, weighed and processed for routine histology (fixed in 10% formalin, paraffin-embedded, sectioned to 6 µm, and hematoxylin and eosin stained). Alternatively, implants were extracted and assayed for alkaline phosphatase activity.

What is claimed is:

1. A method for inducing chondrogenesis in vivo in joint tissue comprising the step of exposing said tissue to a composition comprising growth and differentiation factor-5 in an extracellular matrix consisting of type II collagen.

2. A composition comprising an effective amount of growth and differentiation factor-5 sufficient to induce chondrogenesis in vivo in joint tissue in an extracellular matrix consisting of type II collagen.

3. The composition according to claim 2 wherein said effective amount is in the range of about 1 to 10 mg/ml of matrix.

* * * * *

UNITED STATES PATENT AND TRADEMARK OFFICE
CERTIFICATE OF CORRECTION

PATENT NO.      : 6,849,606 B2
DATED           : February 1, 2005
INVENTOR(S)     : Heidaran et al.

It is certified that error appears in the above-identified patent and that said Letters Patent is hereby corrected as shown below:

<u>Title page,</u>
Item [56], References Cited, U.S. PATENT DOCUMENT: add
-- 6,586,406 B1     07/2003     Heidaran et al………..514/21 --

Signed and Sealed this

Twenty-fourth Day of May, 2005

JON W. DUDAS
*Director of the United States Patent and Trademark Office*